United States Patent [19]

Haapamäki

[11] 4,344,321

[45] Aug. 17, 1982

[54] SLURRY MEASURING APPARATUS

[75] Inventor: Pertti Haapamäki, Beaconsfield, Canada

[73] Assignee: Rauma-Repola Oy, Finland

[21] Appl. No.: 175,007

[22] Filed: Aug. 4, 1980

[30] Foreign Application Priority Data

Aug. 24, 1979 [CA] Canada .................................. 334392

[51] Int. Cl.³ .......................................... G01N 15/04
[52] U.S. Cl. .......................................... 73/61.4; 73/63
[58] Field of Search ........................ 73/61.4, 63, 61 R

[56] References Cited

U.S. PATENT DOCUMENTS

| 910,002 | 1/1909 | Klemm et al. | 73/63 |
| 2,346,945 | 4/1944 | Samson et al. | 73/63 |
| 3,838,594 | 10/1974 | Kesler | 73/61 R |

FOREIGN PATENT DOCUMENTS 342574 10/1921 Fed. Rep. of Germany .......... 73/63

Primary Examiner—Kyle L. Howell
Assistant Examiner—Joseph W. Roskos
Attorney, Agent, or Firm—Burns, Doane, Swecker & Mathis

[57] ABSTRACT

An apparatus and method is disclosed for experimental displacement of liquids in slurries for measuring filtration rate, washing performance and displacement bleaching in pulp. An open top cylinder is movable to a vertical orientation and has a piston slidably positioned therein. The piston includes a porous face with communicating passages to its rear surface. Apparatus are provided for registering pressure in the cylinder as well as for providing regulated motion of the piston. Also, a valve is provided for admitting wash water to the lower part of the cylinder for back washing the filter cake.

3 Claims, 2 Drawing Figures

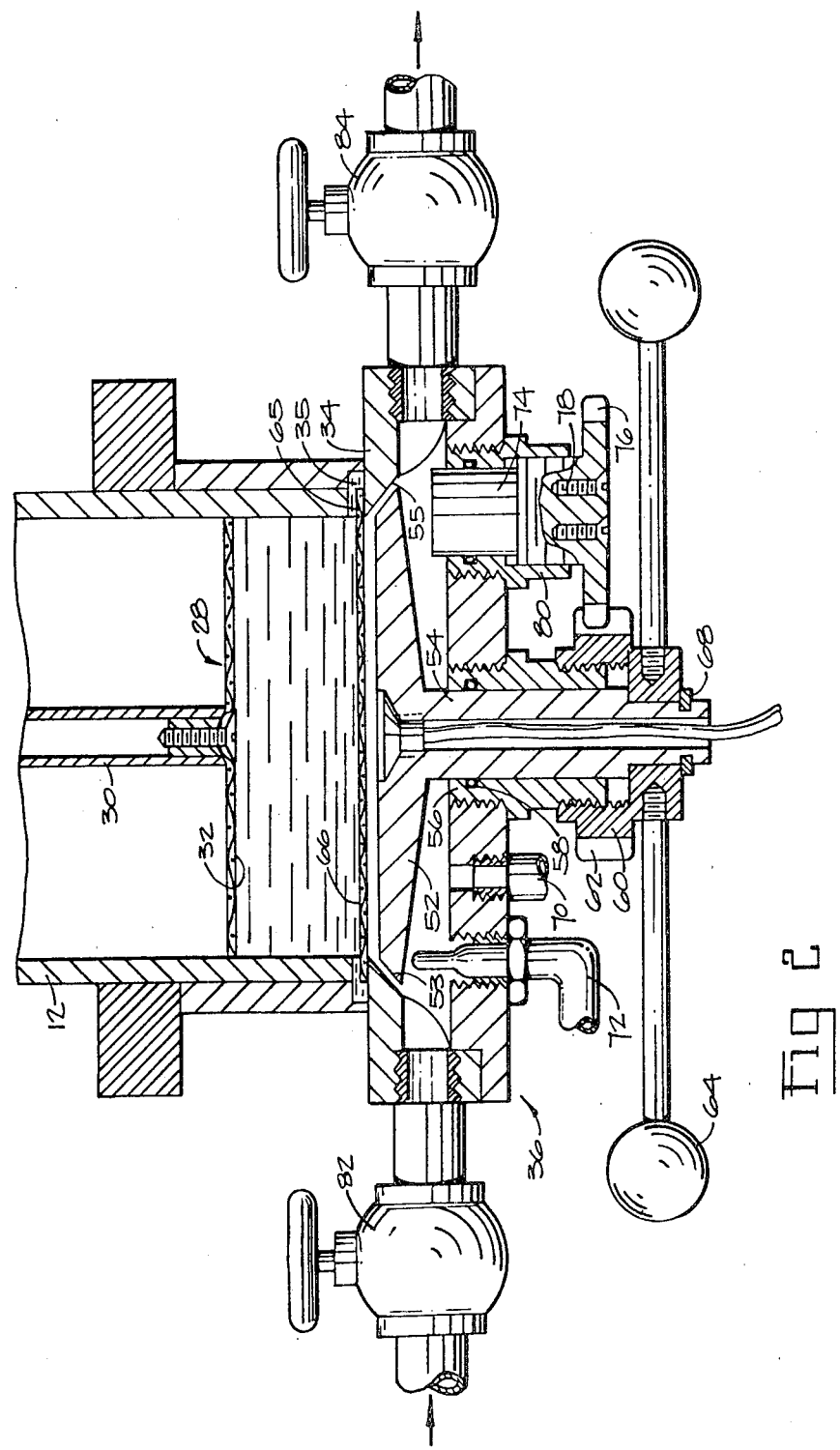

SLURRY MEASURING APPARATUS

This invention relates to an instrument or device for measuring the drainage and washing characteristics of suspensions of solids in liquids such as paper making pulp and other slurries.

In known devices, attempts have been made to obtain meaningful results by measuring related properties such as "freeness" or the rate of accumulation of a filter cake on a filter leaf. Although these measurements have been of some value, they have been deficient in several respects and in some cases where air is entrained in the material, the results are questionable. The present invention provides a device for providing a drainage to remove excess liquid from the slurry and to provide means for subsequently washing the filter cake. According to the present invention, means are provided to ensure that entrained air is not lost and furthermore that the measurement obtained can be performed rapidly so that conditions are not permitted to change as a result of coalescence of air bubbles.

The present invention provides the formation of a uniform filter cake with minimal edge effects. Generally speaking, with a filter cake formed under conventional conditions as on a filter leaf under vacuum, there is a tendency for the periphery to contract resulting in a nonuniform flow through the cake. Such a contraction on the edge can alter a measurement which is intended to simulate performance on production filters and washers where edge effects are negligible because of the relatively large draining areas involved.

According to one aspect, the invention relates to a method of measuring slurry filtration rate comprising retaining a slurry sample in an enclosed cylinder and moving a close fitting piston provided with a filtering means downwardly in said cylinder and allowing accumulation of filtrate behind the piston, the motion of the piston creating a drainage pressure difference and during said measurement, registering pressure in the cylinder and motion of the piston.

In accordance with another aspect, the invention relates to apparatus comprising a cylinder suitably adapted to be tilted from a vertical to a horizontal position and beyond; a piston slidably positioned in the cylinder, said piston having a porous face to retain solids but to provide communication for liquid between the face of the piston and the rear thereof; a porous member positioned to cover one end of the cylinder; a chamber secured to the cylinder outwardly of said porous member; and the end wall of the cylinder outwardly of the porous member being mounted in said chamber with its surface being in juxtaposition to the surface of said porous member and adapted for linear movement within the chamber toward and away from fully closed or fully opened positions relative to said porous member; and means for selectively positioning the end wall of said cylinder relative to the porous member; and valve means in the chamber for drainage thereof or admission of liquids therein.

In its simplest form, the measurement of drainage rate would be carried out by having a sample of slurry transferred to the vertically oriented cylinder, the piston being inserted therein and arranged to travel down into the slurry so that suspended solids accumulate on the filter and filtrate flows through the filter and accumulates behind the piston. The piston travel can be regulated either manually or automatically to maintain a constant pressure differential or constant speed of the piston in accordance with the desired experiment.

The arrangement of a "filter piston" travelling vertically downward provides a means of ensuring that suspended air in the slurry is carried through the filter cake as would occur in a commercial filter. The apparatus also provides a convenience for rapid execution of the experiment and accurate maintenance of pressure differential through the compensating action of filtrate accumulated behind the piston which thereby maintains total liquid head constant during the experiment.

Washing experiments can also be performed with the present invention by (a) forming a filter cake as described above, the cake being compressed to a predetermined thickness using a suitable insert to limit piston travel. After discarding a filtrate that accumulates behind the piston, wash water is introduced in the bottom of the cylinder and passed through the filter cake to create a single stage displacement washing. Additionally, several liquids, arranged contiguously in series, may be passed through the filter cake to simulate multistage washing or dynamic bleaching.

The apparatus of the present invention provides a uniform drainage flow of wash liquid over the whole area of the filter cake due to the movable end wall of the cylinder. Measurements representative of actual pulp conditions are provided and because of the rapidity of the test, air is not lost. Additionally, the arrangement of the apparatus provides for evaluating performance and effect of various factors such as flow rate, temperature, consistency, etc.

A further advantage of the present invention is the simplicity of the means of maintaining a required pressure differential during drainage evaluations, a further advantage being that it is suitable for performing evaluations of washing performance in either single stage or multistage arrangements.

The invention is illustrated by way of example in the accompanying drawings wherein:

FIG. 2 is a fragmentary sectionalized view of the lower end of the cylinder arrangement.

Figure 1:
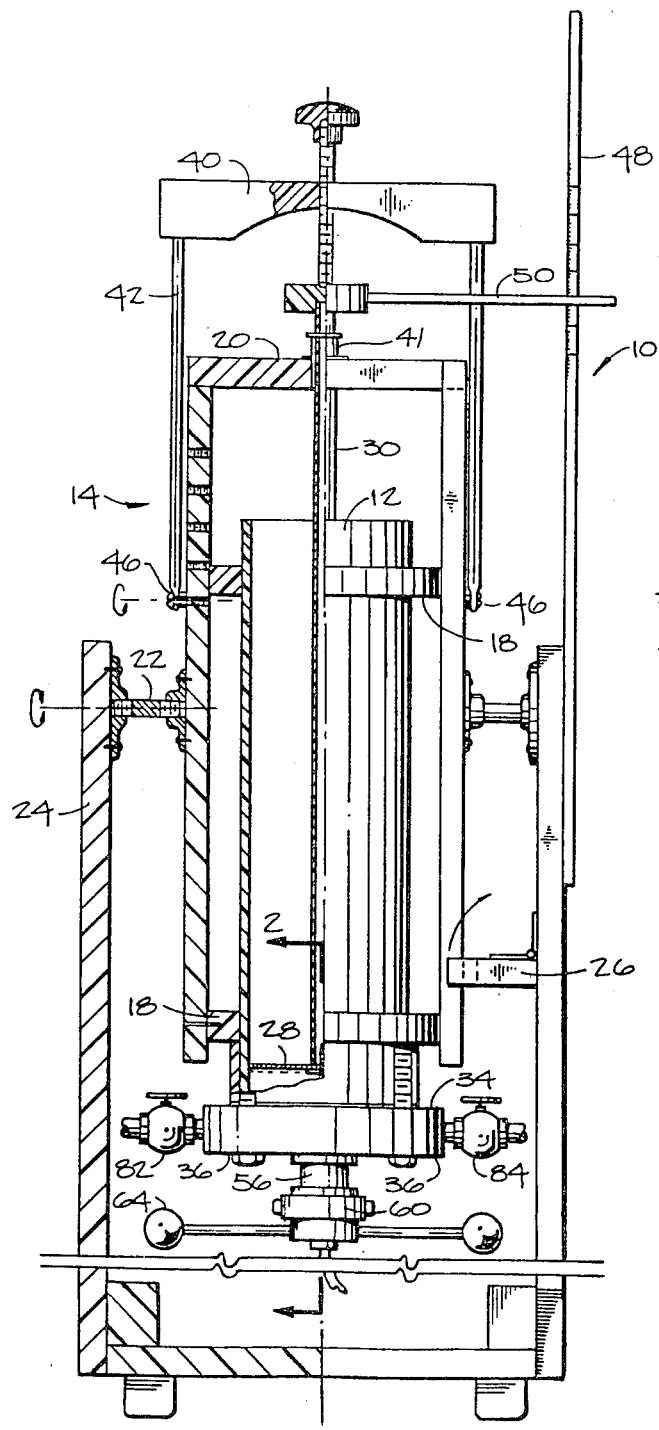
FIG. 1 is an elevation view partly in section of the apparatus.

Referring to FIG. 1, the instrument 10 comprises an elongated cylinder 12 mounted in a frame 14 having side members 16, cylinder locating collars 18 and a yoke 20 bridging the side members 16. The latter are pivotally mounted such as by pins 22 to a suitable support framework 24 so that the instrument can be placed on a level surface. By virtue of its pivotal mounting, the frame 14 can be locked into the illustrated, vertical position by means of a pivotal latch 26 mounted on one of the support member legs as shown.

A piston 28 is slidably positioned within the cylinder 12 and is provided with an elongated piston rod 30 positioned in the yoke 20, the piston 28 comprising a perforated disc 32 as shown in FIG. 2. The lower end of the cylinder 12 is detachably secured to the rim 34 of a chamber 35 (FIG. 2) by means of bolts 38 extending through the walls of the chamber 36 and into the cylinder support collar 18. The depth to which the piston is to be moved relative to the other end of the cylinder can be altered by means of adjusting a pin 41 in the rod 30 relative to the upper surface of the yoke 20 of the frame 14. Arms 42 attached to an upper cross member are pivotally positioned in the side members 16 by means of suitable screws 46. Suitable measuring means can be provided in the form of a graduated member 48 mounted on the support 24 and cooperating indicator 50 suitably positioned on the piston rod 30.

Referring now to FIG. 2, the lower end of the cylinder 12 is provided with a filter screen 66, the peripheral edge 65 thereof resting on the rim 34 of the chamber 36 and under a seal 35. Chamber 36 encloses the circular end wall 52 of the cylinder, wall 52 having an elongated stem 54 extending downwardly through the lower end of the chamber 36. Stem 54 is positioned within the nipple 56 incorporating an O-ring 58 on the upper end thereof to seal the stem 54 from the interior of the chamber 36.

Nipple 56 has an exteriorly threaded portion to receive threaded ring gear 60 having a series of external, circumferential gear teeth 62 thereon. Ring gear 60 is provided with a suitable handle 64 for rotation thereof and, due to the connection of the ring 60 to the lower end of the stem 54 by means of a spring clip 68, rotation of the handle 64 and the ring gear 62 will move the gear upward or downward in the nipple 56 and at the same time, this vertical movement will be imparted to stem 54 and the end wall 52 of the cylinder.

While the end wall 52 is shown with an angular edge 53 for engagement with a mating edge 55 of the chamber 36, this edge configuration is not essential as a straight edge approximately 90° to the face of the end wall 52 is acceptable as long as the end wall 52 can be brought up to a closed position with respect to the screen 66 so that there is zero clearance between screen 66 and the end wall 52 when the latter is in the closed position.

As illustrated, the chamber 36 may be provided with a pressure gauge 70 and a thermometer or temperature indicator 72. In addition, although it is not an essential element, the chamber can also be provided with a movable equalizer 74 adapted to provide compensation within the chamber 36 for the volume of the stem 54 of the wall 52. As shown, this equalizer 74 can be interconnected to the ring gear 60 by means of a driven gear 76 secured to the lower end of a plug 78 which threadably engages the interior of a nipple 80, plug 78 being interconnected to the equalizer 74. Accordingly, when the wall 52 is raised upwardly, the equalizer 74 will be lowered and vice versa.

The chamber 36 is also provided with a pair of valves 82, 84 for the admission and drainage of flushing liquid, chemical bleach, etc.

It will be appreciated from the above description that a slurry sample 75 is placed in the cylinder 12 and the close fitting piston 28 with its perforated disc 32 is placed in the cylinder on top of the slurry and is moved downwardly under a controlled rate either by its own weight or by manual or motion transmitting means, not shown. As the slurry comes under pressure, the filtrate moves through the face 32 of the piston and accumulates on the rear face thereof and when desired, with the end wall 52 open and valve 84 open filtrate can also pass through the screen of the filter plate 66. When the desired cake is formed on the lower filter plate 66, the cylinder can be pivoted beyond the horizontal to drain the filtrate therefrom. If it is desired to treat the filter cake now formed, the bottom wall 52 can be moved downwardly, water or other liquid can be admitted into the chamber 36 through valve 82.

While the invention has been described in connection with a specific embodiment thereof and in a specific use, various modifications thereof will occur to those skilled in the art without departing from the spirit and scope of the invention as set forth in the appended claims.

The terms and expressions which have been employed in this specification are used as terms of description and not of limitation and there is no intention in the use of such terms and expressions to exclude any equivalents of the features shown and described or portions thereof, but it is recognized that various modifications are possible within the scope of the invention as claimed.

The embodiments of the invention in which an exclusive property or privilege is claimed are defined as follows:

1. Apparatus comprising a cylinder suitably adapted to be tilted from a vertical to a horizontal position and beyond; a piston slidably positioned in the cylinder; said piston having a porous face to retain solids but to provide communication for liquid between the face of the piston and the rear thereof; a porous member positioned to cover one end of the cylinder; a chamber secured to the cylinder outwardly of said porous member; and the end wall of the cylinder outwardly of the porous member being mounted in said chamber with its surface being in juxtaposition to the surface of said porous member and adapted for linear movement within the chamber toward and away from fully closed or fully opened positions relative to said porous member; and means for selectively positioning the end wall of said cylinder relative to the porous member; and valve means in the chamber for drainage thereof or admission of liquids therein.

2. Apparatus according to claim 1 including means for equalizing volume in the said chamber as may be required to compensate for volume change resulting from movement of the said end wall.

3. Apparatus according to claim 1 wherein, when the end wall is moved to its closed position relative to the porous member, there is zero clearance between the juxtaposed surfaces.

* * * * *